United States Patent
Mateu et al.

(10) Patent No.: US 11,612,557 B1
(45) Date of Patent: Mar. 28, 2023

(54) LYOPHILIC COLLOIDS

(71) Applicant: Jeen International Corp., Fairfield, NJ (US)

(72) Inventors: Juan R Mateu, Ottawa, IL (US); Mackenzie Nunn, Newton, NJ (US); Oscar Ortiz-Gutierrez, Plainfield, NJ (US); Adam Perle, Miami, FL (US)

(73) Assignee: Vantage Specialty Ingredients, Inc., Warren, NJ (US)

( * ) Notice: Subject to any disclaimer, the term of this patent is extended or adjusted under 35 U.S.C. 154(b) by 0 days.

(21) Appl. No.: 17/864,410

(22) Filed: Jul. 14, 2022

Related U.S. Application Data

(60) Provisional application No. 63/327,080, filed on Apr. 4, 2022, provisional application No. 63/322,654, filed on Mar. 23, 2022, provisional application No. 63/221,955, filed on Jul. 15, 2021.

(51) Int. Cl.
| | |
|---|---|
| *A61K 8/02* | (2006.01) |
| *A61K 8/73* | (2006.01) |
| *A61K 8/04* | (2006.01) |
| *A61K 8/34* | (2006.01) |
| *A61K 8/92* | (2006.01) |
| *A61K 8/99* | (2017.01) |
| *A61Q 19/00* | (2006.01) |
| *A61K 8/81* | (2006.01) |

(52) U.S. Cl.
CPC .............. *A61K 8/735* (2013.01); *A61K 8/042* (2013.01); *A61K 8/345* (2013.01); *A61K 8/73* (2013.01); *A61K 8/733* (2013.01); *A61K 8/8176* (2013.01); *A61K 8/92* (2013.01); *A61K 8/99* (2013.01); *A61Q 19/00* (2013.01); *A61K 2800/10* (2013.01); *A61K 2800/30* (2013.01); *A61K 2800/31* (2013.01)

(58) Field of Classification Search
None
See application file for complete search history.

(56) References Cited

U.S. PATENT DOCUMENTS

2021/0052477 A1* 2/2021 Florence ................ A61K 8/671

OTHER PUBLICATIONS

Botanicals, "BP—Triluronic Acid," 2018, pp. 1-4 (Year: 2018).*

* cited by examiner

*Primary Examiner* — Brian Gulledge
(74) *Attorney, Agent, or Firm* — Louis C. Paul & Assoc.

(57) ABSTRACT

A non-Newtonian, lyophilic colloid comprised of (i) at least one anionic, non-sulfated glycosaminoglycan (ANSG) having a molecular weight greater than about 500 kDa and (ii) glycerin.

18 Claims, No Drawings

LYOPHILIC COLLOIDS

CROSS REFERENCE TO RELATED APPLICATIONS

This application claims priority under 35 U.S.C. § 119(e) to the following U.S. Provisional Applications: Ser. No. 63/221,955 (filed on Jul. 15, 2021); Ser. No. 63/322,654 (filed on Mar. 23, 2022); and Ser. No. 63/327,080 (filed on Apr. 4, 2022).

FIELD OF INVENTION

Reduced-water content, lyophilic colloids, and their uses in the fields of personal care, dermatology, and other branches of medicine.

BACKGROUND OF THE INVENTION

Many personal care formulations are comprised of about 70 to 90 percent water. But use of water can make achieving environmental sustainability goals, including those set by retailers and consumer packaged goods companies. Water-based products require substantially more energy than anhydrous products—not only in terms of fuel costs for shipping product but also to combine hydrophilic and hydrophobic ingredients to form emulsions. Water-based products require preservation. Eliminating water and providing concentrated products to which water can be added at the time of use, minimizes packaging.

Naturally-occurring or naturally-derived polysaccharides are increasingly preferred in personal care and other consumer packaged goods (also referred to as "finished goods") for their "eco-friendly" and non-toxic properties.

International Patent Application Publication Number WO 2007/102125 filed by the Procter & Gamble Company under the Patent Cooperation Treaty discloses an anhydrous lipophilic personal care compositions (including, specifically, lipsticks) comprised of: (i) 1-30% of a polyglycerin fatty acid ester having a polyglycerin of 2-20 units and at least one branched fatty acid residue of 8 to 22 carbons; (ii) 0.01-6% of glycerin; (iii) a water-soluble skin benefit agent in an amount dissolvable in glycerin; and (iv) a lipophilic carrier that is substantially free of surfactant. This patent application publication also discloses a method of preparing the lipophilic personal care composition by (i) dissolving a water-soluble skin benefit agent into glycerin; (ii) dissolving the product of step (i) into the polyglycerin fatty acid ester; and (iii) mixing the product of step (ii) with an anhydrous lipophilic carrier. Polyglycerin fatty acid esters having a polyglycerin of 2-20 units and at least one branched fatty acid residue of 8 to 22 carbons are disclosed to include esters made of polyglyceryl-2, olyglyceryl-4, polyglyceryl-6, or polyglyceryl-10; with at least 5 isostearate residues. Water-soluble skin benefit agents are listed to include sodium alginate, sodium hyaluronate, and carrageenan. Among a list of water-soluble polymers that are taught to be suitable for addition to the composition are xanthan gum and a modified cellulose polymer (sodium carboxmethyl cellulose).

The non-Newtonian, Lyophilic Colloids of the present invention disclosure differ from the anhydrous lipophilic personal care compositions disclosed in WO 2007/102125 in several important respects: the minimum glycerin content of the inventive non-Newtonian, Lyophilic Colloid is at least 20%—more than 3-times the maximum disclosed in WO 2007/102125; the inclusion, in several embodiments of, one or more surfactants; the exclusion, in certain embodiments, of polyglycerin fatty acid ester having a polyglycerin of 2-20 units and at least one branched fatty acid residue of 8 to 22 carbons (as well as the additional step of dissolving a mixture of the water-soluble skin benefit ingredient into such polyglycerin fatty acid ester).

US Pre-Grant Patent Application Publication 2021/0052477 filed by Mary Kay, Inc. is directed to reducing the appearance of facial fine lines and wrinkles (forehead creases, between-the-brow creases, crow's feet, smile lines, vertical lip lines, and marionette lines) both immediately and over a period of time with a topical composition comprised of (i) an oleo gum resin (ii) glycerin, and (iii) ANSG or an ANSG salt. The compositions can include water, but are also taught to be substantially anhydrous and anhydrous. See ¶ [0014]. The resin fills the wrinkle creases and hyaluronic acid attracts water to the wrinkle, thereby reducing the appearance of a wrinkle immediately after application to skin. See ¶ [0006]. Long-lasting reduction of the appearance of wrinkle (e.g., over time) is accomplished by other ingredients (e.g., retinal). While this publication generally discloses and lists a wide range of ingredients that can be included in the topical compositions for reducing the appearance of facial fine lines and wrinkles—UV absorption agents, moisturizing agents, antioxidants, structuring agents, emulsifiers, silicone-containing compounds, essential oils, thickening agents (including alginates, carrageenan and cellulose), and preservatives—there are no specific teachings or suggestions of use levels (concentrations), or which ingredients can/should be combined, and in what ratios.

U.S. Pat. No. 9,855,206 ("the '206 Patent") relates to alcogels formed by combining hyaluronic acid with a polyhydric alcohol and a polycarboxylic acid or oxycarbonic acid. More particularly, the '206 Patent is directed to hyaluronic acid gel sheets having a thickness ranging from 30 μm to 1 mm and containing three ingredients in specific ratios: (i) 100 parts of hyaluronic acid having a molecular weight of from $5 \times 10^4$ to $5 \times 10^6$ Daltons, (ii) 10 to 100 parts by weight of polycarboxylic acid or oxycarbonic acid, and (iii) 100 to 8000 parts by weight of polyhydric alcohol. These ratios are important to achieving a gel strip having flexibility, elasticity, tensile strength, skin adherence. The non-Newtonian Lyophilic Colloids of the present invention disclosure differ from the above-described hyaluronic acid gel sheets in several respects including the absence of polycarboxylic acid or oxycarbonic acid.

There has been and remains a need for more sustainable (reduced water content) ingredients and finished formulations containing a naturally occurring or naturally derived ingredients that provide benefits to the skin and hair/scalp. Those needs are met by the non-Newtonian, lyophilic colloids of the present invention disclosure.

SUMMARY OF THE INVENTION

Non-Newtonian, Lyophilic Colloids comprised of, consisting essentially of, or consisting of at least one anionic, non-sulfated glycosaminoglycan and glycerin.

DETAILED DESCRIPTION OF THE INVENTION

I. Definitions

"Anionic, non-sulfated glycosaminoglycan" (ANSG) that are an integral part of Lyophilic Colloids of the present invention are polymer chains comprised of repeating disaccharide monomers -D-glucuronic acid and D-N-acetylglucosamine—that attach to each other through beta-1,4 glycosidic bonds, and can have a molecular weight ranging from 1 kDa to over 2,000 kDa. Within the scope of the present invention disclosure ANSGs include hyaluronic acid ("HA") and its alkaline or alkaline-earth salts, with sodium hyaluronate being preferred. HA can be modified, where modification is via synthetic pathways known in the art including as described in: Carbohyd Res. 2020 March; 489:107950; J Cosmet Dermatol. 2016 December; 15(4): 520-526.

"Lyophilic Colloid" is a colloidal system in which the dispersed phase has a high affinity for the dispersion medium. The colloidal nature of the system is confirmed by scattering of light by the ANSG (and/or other polysaccharide) dispersed in glycerin.

By "Non-Newtonian" is meant a rheological behavior in which there is a reduction of viscosity with an increase in shear stress.

By "Substantially Anhydrous" is meant the Lyophilic Colloid contains less than 5% water, preferably less than 2.5% water, more preferably less than 1% water, still more preferably less than 0.5% water, even more preferably less than 0.1% water. "Finished Product" means a formulation (also known in the art as a preparation) that can be applied directly to a keratinous substrate (skin, scalp/hair) or a mucosal membrane (ocular tissue, nasal passage, urogenital tract) or injected.

"At least one" means one or more, and includes individual components as well as mixtures/combinations.

Numbers used in describing quantities of ingredients and/or reaction conditions are to be understood as being modified in all instances by the term "about."

Numerical ranges are meant to include numbers within the recited range, and combinations of subranges between, the given ranges. For example, a range from 1-5, includes 1, 2, 3, 4 and 5, as well as subranges such as 2-5, 3-5, 2-3, 2-4, 1-4, etc.

Unless otherwise indicated, percentages, parts and ratios are to be understood as based upon the total weight of the Lyophilic Colloid or a Finished Product containing the Lyophilic Colloid.

II. Compositions and Methods of Manufacture

The non-Newtonian, Lyophilic Colloids of the present invention are "stable"; and do not undergo syneresis or produce an exudate.

While certain embodiments can and do contain an emulsifier, in certain preferred embodiments, the non-Newtonian Lyophilic Colloids of the present invention do not contain one or both of a polyglycerin fatty acid ester having a polyglycerin of 2-20 units and at least one branched fatty acid residue of 8 to 22 carbons and/or a surfactant.

In other preferred embodiments, the non-Newtonian, Lyophilic Colloids of the present invention do not contain a polycarboxylic acid or an oxycarbonic acid.

The non-Newtonian Lyophilic Colloids of the present invention are comprised of, consist essentially of, or consist of at least one ANSG and glycerin in ratios ranging from about 0.1:99.9 to about 1:1. In certain embodiments, the ratio of the at least one ANSG and glycerin is from about 1:99 to about 1:49.

In some embodiments, the at least one ANSG is present in the non-Newtonian Lyophilic Colloid at a concentration of at least about 0.1%, preferably at a concentration of at least about 0.2%, more at a concentration of at least about 0.3%, still more preferably at a concentration of at least about 0.4%, and even more at a concentration of at least about 0.5%.

In other embodiments, the at least one ANSG is present in the non-Newtonian Lyophilic Colloid at a concentration of at least about 0.75%, preferably at a concentration of at least about 1%, more preferably at a concentration of at least about 1.25%, still more preferably at a concentration of at least about 1.5%, and even more at a concentration of at least about 1.75%.

In still other embodiments, the at least one ANSG is present in the non-Newtonian Lyophilic Colloid at a concentration of at least about 2%, at least about 5%, at least about 10%, at least about 15%, and at least about 20%. In these embodiments, an extrusion mixing process is employed to combine the ANSG and glycerin.

In one embodiment, the non-Newtonian Lyophilic Colloid contains the at least one ANSG at a concentration of greater than 40%.

One or a combination of ANSGs of different molecular weight ranges can be used in forming the non-Newtonian, Lyophilic Colloid of the present invention.

At least one ANSG is "high molecular weight" ("HMW")—having a molecular weight greater than about 500 kDa, preferably greater than about 1,000 kDa, still more preferably from about 1,500 kDa to about 2,000 kDa.

The at least one ANSG can, in certain embodiments, be a combination of a HMW ANSG and either or both of a low molecular weight ("LMW") ANSG—having a molecular weight of less than 25 kDa, preferably less than about 15 kDa, from about 1 kDa to 10 kDa—or medium molecular weight ("MMW") ANSG—having a molecular weight ranging from about 25 kDa to about 500 kDa.

Surprisingly and unexpectedly, non-Newtonian, Lyophilic Colloids containing a LMW ANSG and/or a MMW ANSG can be perceived as gritty, while those containing a HMW ANSG are not.

Surprisingly, a combination of a HMW ANSG and one or both of LMW ANSG and MMW ANSG produces a non-Newtonian, Lyophilic Colloid that is not perceived as gritty.

In one embodiment, the non-Newtonian, Lyophilic Colloid contains (a) at least one HMW ANSG and (b) at least one LMW ANSG and/or MMW ANSG in a ratio of from about 19:1 to 1:19.

In another embodiment, the non-Newtonian, Lyophilic Colloid contains (a) at least one HMW ANSG and (b) at least one LMW ANSG and/or MMW ANSG in a ratio of from about 9:1 to 1:9.

In still another embodiment, the non-Newtonian, Lyophilic Colloid contains (a) at least one HMW ANSG and (b) at least one LMW ANSG and/or MMW ANSG in a ratio of from about 7:3 to 3:7.

In a yet another embodiment, the non-Newtonian, Lyophilic Colloid contains (a) at least one HMW ANSG and (b) at least one LMW ANSG and/or MMW ANSG in a ratio of from about 4:1 to 1:4.

In a further embodiment, the non-Newtonian, Lyophilic Colloid contains (a) at least one HMW ANSG and (b) at least one LMW ANSG and/or MMW ANSG in a ratio of from about 2:1 to 1:2.

In one preferred embodiment, the non-Newtonian, Lyophilic Colloid contains (i) a HMW ANSG, (ii) a MMW ANSG, (iii) a LMW ANSG in ratios of from 18:1:1 to 2:1:1.

In another preferred embodiment, the non-Newtonian, Lyophilic Colloid contains (i) a HMW ANSG, (ii) a MMW ANSG, (iii) a LMW ANSG is a ratio of 1:1:1. A blend of three molecular weight ranges of hyaluronan—HMW, MMW and LMW—in ratio of 1:1:1 is commercially available from Botanicals Plus, LLC (distributed by Jeen International, Corp. (Fairlawn, N.J.) under the tradename Triluronic®).

Non-Newtonian, Lyophilic Colloids are formed by combining at least one ANSG and glycerin with mixing at a temperature above room temperature (e.g., about 25° C.).

Combining the ANSG and glycerin at temperatures higher than room temperature accelerates formation of the non-Newtonian, Lyophilic Colloid and is preferred.

In some preferred embodiments, the at least one ANSG is added to glycerin at a temperature of at least 40° C. with mixing.

In other preferred embodiments, the at least one ANSG is added to glycerin at a temperature of at least 50° C. with mixing.

In still other preferred embodiments, the at least one ANSG is added to glycerin at temperature of at least about 70° C. with mixing.

The at least one ANSG can be added to glycerin as a powder or as a hydrogel.

The non-Newtonian, Lyophilic Colloids of the present invention have a water content of less than about 40%.

In some preferred embodiments, the non-Newtonian, Lyophilic Colloids of the present invention have a water content of less than about 20% and are bacteriostatic.

In preferred embodiments, the non-Newtonian, Lyophilic Colloids of the present invention are substantially anhydrous (as defined above).

In certain embodiments, the non-Newtonian, Lyophilic Colloids are preferably "substantially preservative free"—by which is meant it contains less than 0.25% of one or more ingredients that retard the growth of and/or kill bacteria, yeasts and/or molds.

In embodiments in which the ANSG is a hydrogel, it is preferably mixed and heated to reduce (evaporate) water content.

The non-Newtonian, Lyophilic Colloid may be prepared by using conventional mixing techniques and equipment known to the person having ordinary skill in the art (e.g., blenders; stirrers; mixers, agitators and homogenizers including high shear mixers from Silverson Machines, Inc., East Longmeadow, Mass., Heavy Duty Continuous Process Mixer from Readco Kurimoto, LLC, York, Pa.).

Non-Newtonian, Lyophilic Colloids of the present invention may contain an alginate and/or a polysaccharide selected from the group of gums (preferably xanthan gum), carrageenans, and modified cellulose polymers.

"Alginates" are anionic polysaccharides primarily extracted from brown algae (class Phaeophyccae) comprised of β-D-mannuronic acid and α-L-guluronic acid. As used in the present application, the term alginate is to be understood as including salts of alginic acid. Alginates can be homopolymeric sequences of mannuronic acid (M blocks) homopolymeric sequences of guluronic acid (G blocks) and mixed sequences of mannuronic acid and glucuronic acid (MG blocks). Common algal sources of alginates include *Laminaria digitata, Ecklonia maxima, Macrocystis pyrifera, Lessonia nigrescens, Ascophyllum nodosum, Laminaria japonica, Durvillea antartica, Durvillea potatorum* and *Laminaria hyperborea*.

"Gums" are polysaccharides exuded by plants that are gelatinous when moist but hardens on drying to form a resinous substance. Gums can be exudates directly from plants or aqueous solutions or suspensions of the exudates, exudates that have undergone fractionation (e.g., filtration or centrifugation), thermal treatment, spray drying, enzymatic treatment or chemical derivatization. Preferred but not limiting gums include Xanthan Gum, *Astragalus gummifer* (Tragacanth) Gum, *Cyamopsis tetragonoloba* (Guar) Gum, Carob Gum (also known as Carob Seed Gum, Carob Bean Gum, Locust Bean Gum), Gum Arabic (from *Acacia senegal* or *Acacia seyal*), and *Juniperus phoenicea* Gum Extract. Tara Gum, Karaya Gum, Ghatti Gum, Cherry Gum, Apricot Gum, Tamarind Gum, Mesquite Gum, Larch Gum, *Psyllium*, or Fenugreek Gum can also be used.

"Carrageenans" are polysaccharides extracted from red seaweed (Rodophyceae) and includes its salts Calcium Carrageenan, Potassium Carrageenan and Sodium Carrageenan.

Modified cellulose polymers include, but are not limited to, Carboxymethyl Hydroxyethylcellulose, Cellulose Gum, Cellulose Acetate Propionate Carboxylate, Ethylcellulose, Hydroxybutyl Methylcellulose, Hydroxyethylcellulose, Hydroxyethyl Ethylcellulose, Hydroxypropylcellulose, Hydroxypropyl Methylcellulose, Methylcellulose, and Methyl Ethylcellulose.

In embodiments in which the non-Newtonian, Lyophilic Colloid contains (further comprises, further consists essentially of, or further consists of) an alginate, the alginate is combined with water (preferably, in a ratio of at least 1 part water to 99 parts alginate, more preferably at least 2 parts water to 98 parts alginate, still more preferably at least 5 parts water to 95 parts alginate) prior to addition to the non-Newtonian, Lyophilic Colloid.

In certain embodiments, the alginate is combined with water (preferably, in a ratio of at least 1 part water to 99 parts alginate, more preferably at least 2 parts water to 98 parts alginate, still more preferably at least 5 parts water to 95 parts alginate), forming a hydrated alginate, which is then added to glycerin and mixed under heat (preferably at a temperature above room temperature, more preferably at a temperature of at least 40° C.) until homogenous.

In other embodiments, the alginate is combined with glycerin, forming a dispersed alginate, which is then combined with water (preferably, in a ratio of at least 1 part water to 99 parts alginate, more preferably at least 2 parts water to 98 parts alginate, still more preferably at least 5 parts water to 95 parts alginate) and mixed under heat (preferably at a temperature above room temperature, more preferably at a temperature of at least 40° C.) until homogenous.

In still other embodiments, the alginate is combined with a hydroglycolic solution comprised of glycerin and water (preferably, in a ratio of at least 1 part water to 99 parts alginate, more preferably at least 2 parts water to 98 parts alginate, still more preferably at least 5 parts water to 95 parts alginate) and mixed under heat (preferably at a temperature above room temperature, more preferably at a temperature of at least 40° C.) until homogenous.

In one preferred embodiment, the non-Newtonian, Lyophilic Colloid is comprised of, consists essentially of, or consists of an ANSG that is sodium hyaluronate and an alginate that is sodium alginate, where the ratio of ANSG to alginate is about 2:1.

In embodiments in which the non-Newtonian, Lyophilic Colloid of the present invention contains (further comprises, further consists essentially of, or further consists of) at least one polysaccharide other than an alginate—a gum, a carrageenan, and/or a modified cellulose—the at least one polysaccharide is present at a concentration of from about 0.1% to about 5%.

In embodiments in which the non-Newtonian, Lyophilic Colloid of the present invention contains (further comprises, further consists essentially of, or further consists of) an alginate and one or more polysaccharides selected from the group of gums, carrageenans, and modified cellulose polymers, the alginate and polysaccharide(s) are present in the non-Newtonian, Lyophilic Colloid at a combined concentration of from about 0.1% to about 10%.

III. Functional Ingredients

A wide range of ingredients known to the person having ordinary skill in the art of formulating topically applied compositions—personal care, skin care, hair care, and dermatologic—can be included in non-Newtonian, Lyophilic Colloids of the present invention, including surfactants and emulsifiers; alcohols (including glycols); thickening agents; film formers (e.g., polyvinyl pyrrolidone); oils, saponified oils (e.g., of sunflower or safflower), esters, fatty alcohols (Cetearyl Alcohol; Cetyl Alcohol; Stearyl Alcohol) and other emollients and conditioning agents; as well as ingredients that confer one or more benefits to a keratinaceous substrate (e.g., skin or hair), so-called "active" ingredients. These functional ingredients can be present at concentrations of up to about 50% by weight of the Lyophilic, Colloid.

Non-limiting examples of surfactants that can be added to non-Newtonian, Lyophilic Colloids of the present invention include: Cocoamidopropyl Betaine; Sodium Cocoyl Isethionate; Sodium Lauroamphoacetate; Sodium Methyl Cocoyl Taurate; Sodium Lauryl Sulfate (SLS); Sodium Laureth Sulfate (SLES). In certain preferred embodiments, the surfactant is neither SLS nor SLES. Surfactants can be cationic (e.g., Stearamidopropyl Dimethylamine).

Emulsifiers that can be included in the non-Newtonian, Lyophilic Colloids of the present invention include: oil-in-water emulsifiers (e.g., Ceteareth-20); silicone-in-water emulsifiers (e.g., PEG-12 Dimethicone); water-in-oil emulsifiers (e.g., PEG-IO Stearate; Polyglyceryl-4 Oleate, commercially available as JEECHEM® 100 from JEEN International Corp.); water-in-silicone emulsifiers (e.g., PEG/PPG-30/10 Dimethicone or Lauryl PEG/PPG-18/18 Methicone). Emulsifiers can be cationic, anionic, non-ionic, or amphoteric and are preferably used in gel and film embodiments of the present invention.

Two non-limiting, but preferred, examples of multi-functional, cationic, conditioning emulsifiers that can be included in the Lyophilic Colloid are Behentrimonium Methosulfate, Behentriumonium Chloride, Stearamidopropyl Dimethylamine, or Cetrimonium Chloride.

"Active ingredients" may be incorporated in the non-Newtonian, Lyophilic Colloids at a concentration of at least about 0.01%, more preferably at a concentration of at least about 0.01%, preferably at a concentration of at least about 0.1%, more preferably at a concentration of at least about 0.25%, still more preferably at a concentration of at least about 0.5%, and even more preferably at a concentration of at least about 1.0% by include: agents for the treatment of an inflammatory dermatosis, including acne, psoriasis or rosacea; anti-microbial and anti-fungal actives; anti-itch agents; topical anaesthetics; sunscreens; emollients and skin soothing agents; non-steroidal anti-inflammatory agents; humectants and moisturizing agents, in addition to hyaluronic acid, and, if present, glycols; skin barrier protectants; lipids and ceramides, including vegetal-derived oils and butters; exfoliants and desquamatory agents; glucosides; antioxidants and agents that reduce the appearance of fine lines and wrinkles, including vitamins, proteins and peptides; skin bleaching and lightening agents; lysates of microorganisms; and plant extracts.

"Active ingredients" may be in a solvent or "extraction vehicle" known to the skilled artisan which include, but are not limited to, lower alcohols (methanol, ethanol), hydro-alcoholic solutions, and glycols.

In certain embodiments, the active ingredient may also be encapsulated.

Preferred but non-limiting examples of vegetal-derived oils and butters include: Apricot Oil; Avocado Oil; Canola Oil; Castor Oil; Coconut Oil; Cottonseed Oil; *Eucalyptus* Oil; Evening Primrose Oil; Flaxseed Oil; Grape Seed Oil; Jojoba Oil Lavender Oil; Macadamia Nut Oil; Olive Oil; Peppermint Oil; Rice Bran Oil; Safflower Oil; Sesame Oil; Soybean Oil; Sunflower Oil; Sweet Almond Oil; Tea Tree Oil; Wheat Germ Oil; Cocoa Butter; and Shea Butter.

Preferred vitamins and vitamin derivatives include, but not limited to Ascorbic Acid and its esters Ascorbyl Palmitate and Magnesium Ascorbyl Phosphate; Tocopherol and its esters Tocopheryl Acetate; Retinal and its Ester, Retinyl Palmitate; Retinaldehyde; Panthenol and Niacinamide.

Preferred skin lightening ingredients include, but are not limited to, Arbutin, Hydroquinone, Kojic Acid, Ascorbic Acid, Magnesium Ascorbyl Phosphate and Ascorbyl Glucosamine.

"Lysates" of microorganisms can also be included in the non-Newtonian, Lyophilic Colloids of the present invention. Lysates are not "viable"; they do not have the ability to actively grow and divide. Microbial viability can be determined using imaging assays known to the skilled artisan, including assays that measure membrane permeability and DNA binding. Bacterial viability is assessed using membrane permeant and impermeant DNA dyes, including Fluorescein Isothiocyanate (FITC) and Sulforhodamine 101 Acid Chloride (also known as "Texas Red®"), and fluorescent labels, including Hexidium Iodide, Promidium Iodide, and Ethidium Homodimer-2. Yeast cell viability is assessed using FITC and 4',6-diamidino-Calcofluor White M2R as a fluorescent signal.

Non-limiting examples of lysates of microorganisms include: yeast hydrolysate, biofermented by *Lactobacillus* strain, commercially available from BASF Care Creations as Relipidium® A00265 (INCi name: Hydrolyzed Yeast Protein; Butylene Glycol; Pentylene Glycol); ProBioBalance NP (Bifida Ferment Lysate) and ProRenew™ Complex (*Lactococcus* Ferment Lysate) are both available from Chemisches Laboratorium Dr. Kurt Richter GmbH. DERMA-FORCE IQ™, a combination of two lysates—*Lactobacillus* Ferment Lysate and *Saccharomyces* Lysate, commercially available from Bio Component Research.

Lystates can, in certain embodiments, be formed "in situ" by adding probiotics to the non-Newtonian, Lyophilic Colloids of the present invention. "Probiotics" are live (i.e., viable) microorganism intended to have health benefits when consumed or applied to the body. See, www.nccih.nih-.gov/health/probiotics-what-you-need-to-know (accessed on Jul. 4, 2022). Non-limiting examples of probiotics include: (i) Gram positive bacteria selected from the groups of: *Lactobacillus; Bifidobacterium; Staphylococcus*, preferably *Staphylococcus epidermidis; Streptococcus*, preferably *Streptococcus pyogenes; Cutibacteria*, preferably *Cutibacteria avidum*; (ii) yeasts, such as *Saccharomyces boulardii*; and (iii) fungi, such as Malasezzia. Because of the anti-microbial properties of glycerin, when a probiotic is added to non-Newtonian, Lyophilic Colloid it ceases to be viable.

IV. Lyophilic Colloids as Raw Materials and Finished Products

The non-Newtonian, Lyophilic Colloids of the present invention can be raw materials which are combined with one or more other ingredients, including water, an oil, an ester, a silicone and/or one or more "functional ingredients" (described in Section III above) to form a Finished Product.

The non-Newtonian, Lyophilic Colloids of the present invention can also themselves be Finished Products. When administered to the skin or mammalian mucosal tissue (e.g., oral, nasal, ophthalmic, or urogenital), and hydrated through contact with an extrinsic source of water (e.g., when washing) or a water-containing bodily fluid, the non-Newtonian, Lyophilic Colloid can act as a "delivery system" for one or more "functional ingredients" as described in Section III above.

In aesthetic medicine (i.e., cosmetic dermatology and reconstructive/plastic surgery), ANSG—typically modified with 1,4-butanediol diglycidal ether and di-vinyl sulfone as cross-linking agents—can be combined with glycerin forming a non-Newtonian, Lyophilic. Non-Newtonian, Lyophilic Colloids can be injected for:

i. lip augmentation
ii. dermal implantation for correction of perioral rhytids
iii. cheek augmentation to correct age-related volume deficit in the mid-face;
iv. correction of moderate to severe facial wrinkles and folds (e.g., nasolabial folds).

In rheumatology and orthopedics, the non-Newtonian, Lyophilic Colloid of the present invention can be used for intra-articular injection in treatment of osteoarthritis (e.g., of the knees). In these embodiments, the non-Newtonian, Lyophilic Colloid is "activated" when contacted with the synovial fluid within a joint space.

In ophthalmology, the non-Newtonian, Lyophilic Colloid of the present invention is "activated" when contacted with the aqueous humor in the eye.

A non-Newtonian, Lyophilic Colloid of the present invention can alone, or in combination with a substrate (e.g., liner, backing, or woven/non-woven fibrous material), be used as a bandage, wound covering, patch, or mask. When the ANSG is an array of cross-linked hyaluronic acid nanoparticles, the patch can be described as a dissolving "microneedle" patch or mask, even though microneedles per se are not employed.

Substantially anhydrous, non-Newtonian, Lyophilic Colloids can serve as a hygroscopic applicator tip for functional ingredients incorporated in the Lyophilic Colloid, or by wetting (e.g., hydrating) and contacting with a powder (e.g., make-up, a probiotic). In these embodiments, the hydrated tip is applied to a keratinous substrate or a mucosal membrane.

Non-Newtonian, Lyophilic Colloids of the present invention can be in the form of pastes, gels, strips, or films.

V. Examples

The following examples are meant to demonstrate representative Lyophilic Colloids as raw materials per se and Finished Products containing Lyophilic Colloids. They are not meant to be limiting and other examples are possible.

| Example | A | B | C | D | E | F | G | H |
|---|---|---|---|---|---|---|---|---|
| HMWANSG | 0.13 | 0.5 | 0.0 | 0.0 | 0.0 | 0.2 | 0.2 | 0.2 |
| MMWANSG | 0.0 | 0.0 | 0.5 | 0.0 | 2.0 | 0.1 | 0.0 | 0.2 |
| LMW ANSG | 0.0 | 0.0 | 0.0 | 0.5 | 0.0 | 0.0 | 0.1 | 0.2 |
| Glycerin | 99.87 | 99.5 | 99.5 | 99.5 | 98.0 | 94.7 | 97.2 | 98.9 |
| Water | 0.0 | 0.0 | 0.0 | 0.0 | 0.0 | 5.0 | 2.5 | 0.5 |

| Example | I | J | K | L | M | N | O | P | Q |
|---|---|---|---|---|---|---|---|---|---|
| ANSG(s) | 1.0 | 0.4 | 0.4 | 1.6 | 17.0 | 2.0 | 74.4 | 0.0 | 0.0 |
| Glycerin | 96.0 | 98.4 | 99.4 | 78.0 | 64.0 | 94.4 | 1.6 | 0.0 | 0.0 |
| Sodium Alginate | 2.0 | 1.0 | 0.2 | 0.8 | 0.0 | 0.0 | 0.0 | 0.0 | 0.0 |
| Xanthan Gum | 0.0 | 0.0 | 0.0 | 0.0 | 19 | 3.6 | 0.0 | 0.0 | 0.0 |
| Polyvinyl Pyrrolidone | 0.0 | 0.0 | 0.0 | 0.0 | 0.0 | 0.0 | 24.0 | 0.0 | 0.0 |
| Water | 1.0 | 0.2 | 0.0 | 0.0 | 0.0 | 0.0 | 0.0 | 0.0 | 0.0 |

| Example | R | S | T | U | V | W | X |
|---|---|---|---|---|---|---|---|
| Triluronic® A* | 0.1 | 9.0 | 10.0 | 9.4 | 9.1 | 25.9 | 50.0 |
| Glycerin | 99.9 | 82.2 | 80.0 | 75.5 | 72.7 | 64.8 | 50.0 |
| Sweet Almond Oil | 0.0 | 0.0 | 0.0 | 5.7 | 9.1 | 0.0 | 0.0 |
| Cetearyl Alcohol | 0.0 | 6.0 | 0.0 | 0.0 | 0.0 | 9.3 | 0.0 |
| Polyglyceryl 4 Oleate | 0.0 | 2.8 | 0.0 | 0.0 | 0.9 | 0.0 | 0.0 |
| Glycol Stearate | 0.0 | 0.0 | 1.0 | 9.4 | 8.2 | 0.0 | 0.0 |

| Example | AA | BB | CC | DD | EE | FF | GG | HH | II | JJ |
|---|---|---|---|---|---|---|---|---|---|---|
| ANSG(s) | 1.0 | 0.4 | 0.4 | 1.6 | 17.0 | 2.0 | 74.4 | 0.0 | 0.0 | 1.0 |
| Glycerin | QS | QS | QS | QS | QS | QS | QS | QS | QS | QS |
| Sodium Alginate | 2.0 | 1.0 | 0.2 | 0.8 | 0.0 | 0.0 | 0.0 | 0.0 | 0.0 | 2.0 |
| Saccharomyces cerevisiae | 0.25 | 0.0 | 0.0 | 0.0 | 0.0 | 0.0 | 0.0 | 0.0 | 0.0 | 0.0 |
| Lactobacillus acidophilus | 0.0 | 0.50 | 0.0 | 0.0 | 0.0 | 0.0 | 0.0 | 0.0 | 0.0 | 0.0 |
| Bifida Ferment Lysate | 0.0 | 0.0 | 1.0 | 0.0 | 0.0 | 0.0 | 0.0 | 0.0 | 0.0 | 0.0 |

The invention claimed is:

1. A non-Newtonian, lyophilic colloid comprised of (i) at least one anionic, non-sulfated glycosaminoglycan (ANSG) having a molecular weight greater than about 500 kDa and (ii) glycerin.

2. The non-Newtonian, lyophilic colloid of claim 1 containing at least two anionic, non-sulfated glycosaminoglycans, one ANSG having a molecular weight of at least 500 kDa, and one or more ANSGs having a molecular weight less than about 500 kDa.

3. The non-Newtonian, lyophilic colloid of claim 1 that does not contain a polyglycerin fatty acid ester having a polyglycerin of 2-20 units and at least one branched fatty acid residue of 8 to 22 carbons.

4. The non-Newtonian, lyophilic colloid of claim 1 that does not contain a polycarboxylic acid or an oxycarbonic acid.

5. The non-Newtonian, lyophilic colloid of claim 1 in which the at least one ANSG is present at a concentration from about 0.1% to about 20%.

6. The non-Newtonian, lyophilic colloid of claim 5 in which glycerin is present at a concentration from about 20% to about 99.9%.

7. The non-Newtonian, lyophilic colloid of claim 6 further comprising an alginate or a polysaccharide selected from the group of gums, carrageenans, and modified cellulose polymers.

8. The non-Newtonian, lyophilic colloid of claim 6 further comprising at least one functional ingredient selected from the group consisting of (i) surfactants and emulsifiers, (ii) oils and esters and (iii) emollients and conditioning agents, and (iv) ingredients that confer one or more benefits to a keratinaceous substrate.

9. The non-Newtonian, lyophilic colloid of claim 6 that has a water content of less than about 40%.

10. The non-Newtonian, lyophilic colloid of claim 9 that has a water content of less than about 20%.

11. The non-Newtonian, lyophilic colloid of claim 10 that is substantially anhydrous.

12. The non-Newtonian, lyophilic colloid of claim 11 that is substantially preservative free.

13. A method for preparing a non-Newtonian, lyophilic colloid of claim 6 by the steps of adding at the least one ANSG having a molecular weight greater than about 500 kDa to glycerin and mixing at a temperature of at about least 25° C. until homogenous.

14. The method of claim 13 wherein the least one ANSG having a molecular weight greater than about 500 kDa and glycerin are mixed at a temperature of at about least 40° C. until homogenous.

15. The method of claim 13 wherein the non-Newtonian, lyophilic colloid further comprises an alginate, and the alginate is hydrated and is prepared by the steps of (i) adding at least 5 parts water to 95 parts alginate, forming a hydrated alginate; (ii) combining the hydrated alginate of step (i) with glycerin; and (iii) mixing the hydrated alginate in glycerin of step (ii) at a temperature of at least 40° C. until homogenous.

16. The method of claim 13 wherein the non-Newtonian, lyophilic colloid further comprises an alginate, and the alginate is hydrated and is prepared by the steps of (i) adding alginate to glycerin, forming a dispersed alginate; (ii) combining the dispersed alginate of step (i) with water in a water-to-alginate ratio of at least 1:19 and mixing at a temperature of at least 40° C. until homogenous.

17. The method of claim 13 wherein the non-Newtonian, lyophilic colloid further comprises an alginate, and the alginate is hydrated and is prepared by the steps of (i) adding alginate to hydroglycolic solution comprised of glycerin and water wherein the water-to-alginate ratio is at least 1:19 and mixing at a temperature of at least 40° C. until homogenous.

18. The method of claim 13 wherein an alginate and water are added to at least one ANSG having a molecular weight greater than about 500 kDa and glycerin, and the water-to-alginate ratio is at least 1:19.

\* \* \* \* \*